United States Patent
Ryu (10) Patent No.: US 9,250,334 B2
(45) Date of Patent: Feb. 2, 2016

(54) X-RAY DETECTING DEVICE AND X-RAY IMAGING DEVICE USING THE X-RAY DETECTING DEVICE

(75) Inventor: Jea Eun Ryu, Yongin (KR)

(73) Assignee: SAMSUNG DISPLAY CO., LTD., Yongin, Gyunggi-Do (KR)

( * ) Notice: Subject to any disclaimer, the term of this patent is extended or adjusted under 35 U.S.C. 154(b) by 216 days.

(21) Appl. No.: 13/587,352

(22) Filed: Aug. 16, 2012

(65) Prior Publication Data

US 2013/0243155 A1    Sep. 19, 2013

(30) Foreign Application Priority Data

Mar. 16, 2012    (KR) .................. 10-2012-0026973

(51) Int. Cl.
| | | |
|---|---|---|
| *G01T 1/20* | (2006.01) | |
| *G06F 3/033* | (2013.01) | |
| *A61B 6/00* | (2006.01) | |

(52) U.S. Cl.
CPC .................. *G01T 1/2018* (2013.01); *A61B 6/00* (2013.01); *G06F 3/033* (2013.01)

(58) Field of Classification Search
CPC ............. G01T 1/16; G01T 1/24; G01T 1/243; G01T 1/2928; G01T 3/006; G01T 1/2018; G03B 42/02; H05G 1/00; H05G 1/26; G01N 23/04; H04N 5/32; H04N 1/02805; H04N 1/00734; A61B 6/00; A61B 6/462; A61B 6/4233; A61B 6/4494
USPC ............ 378/62, 98, 98.8, 114, 115, 165, 189; 250/370.09
See application file for complete search history.

(56) References Cited

U.S. PATENT DOCUMENTS

| | | | |
|---|---|---|---|
| 2003/0091150 A1* | 5/2003 | Barber et al. ................. | 378/189 |
| 2005/0105688 A1 | 5/2005 | Spahn | |
| 2007/0226656 A1* | 9/2007 | Zwart ........................... | 715/856 |
| 2009/0232273 A1* | 9/2009 | Sendai ............................ | 378/20 |
| 2010/0054416 A1* | 3/2010 | Tsubota et al. ................. | 378/98 |
| 2011/0075811 A1 | 3/2011 | Enomoto | |
| 2011/0110497 A1* | 5/2011 | Nishino et al. ............... | 378/98.8 |

FOREIGN PATENT DOCUMENTS

| | | |
|---|---|---|
| JP | 2004-097471 | 4/2004 |
| KR | 10-2008-0071724 A | 8/2008 |

OTHER PUBLICATIONS

North et al., Acoustic Pulse Recognition Enters Touch-Screen Market, Dec. 2006, Information Display, p. 23.*

(Continued)

*Primary Examiner* — Irakli Kiknadze
*Assistant Examiner* — Julio M Duarte-Carvajalino
(74) *Attorney, Agent, or Firm* — Lee & Morse, P.C.

(57) ABSTRACT

An X-ray detecting device includes a lower case, a driving circuit substrate on the lower case, an X-ray detection panel connected with the driving circuit substrate, the X-ray detection panel being adapted to detect X-rays applied from the outside by converting the X-rays into electricity, a touch panel on the X-ray detection panel, and an upper case on the touch panel. The driving circuit substrate is provided with a driving circuit. The driving circuit is electrically connected with the X-ray detection panel and the touch panel and is adapted to control the driving of the X-ray detection panel and the touch panel.

19 Claims, 9 Drawing Sheets

(56) References Cited

OTHER PUBLICATIONS

Krüger, 2D detectors for particle physics and for imaging applications, Mar. 2005, Elsevier, p. 13-15.*

Kim et al., Construction and characterization of an amorphous silicon flat-panel detector based on ion-shower doping process, 2003, Nuclear Instruments and Methods in Physics Research A vol. 505, p. 56.*

\* cited by examiner

X-RAY DETECTING DEVICE AND X-RAY IMAGING DEVICE USING THE X-RAY DETECTING DEVICE

CROSS-REFERENCE TO RELATED APPLICATIONS

Korean Patent Application No. 10-2012-0026973 filed on Mar. 16, 2012, in the Korean Intellectual Property Office, and entitled, "X-Ray Detecting Device and X-Ray Imaging Device Using the X-Ray Detecting Device," is incorporated by reference herein in its entirety.

FIELD

Embodiments relate to an X-ray detecting device and an X-ray imaging device using the same. In particular, the embodiments relate to an X-ray detecting device including a touch panel.

DESCRIPTION OF THE RELATED ART

X-rays have wavelengths short enough to penetrate objects easily. The amount of penetration of X-rays through an object depends on a density of the object's interior, and an X-ray detecting device is based on such characteristics of X-rays. The X-ray detecting device detects the amount of penetration of X-rays through an object and displays the internal condition of the object through a display device. Such X-ray detecting devices can be used in general as medical examination devices, non-invasive examination devices, etc.

SUMMARY

Embodiments are directed to an X-ray detecting device including a lower case, a driving circuit substrate on the lower case, an X-ray detection panel connected with the driving circuit substrate, the X-ray detection panel being adapted to detect X-rays applied from the outside by converting the X-rays into electricity, a touch panel on the X-ray detection panel, and an upper case on the touch panel, wherein the driving circuit substrate is provided with a driving circuit, and the driving circuit is electrically connected with the X-ray detection panel and the touch panel, and is adapted to control the driving of the X-ray detection panel and the touch panel.

The X-ray detection panel may include a photodetection substrate adapted to convert light into electricity and generate a detection signal, and an optical wavelength conversion member on the photodetection substrate, the optical wavelength conversion member being adapted to convert X-rays applied from an outside into light of a wavelength that can be absorbed by the photodetection substrate.

An adhesive layer may be between the photodetection substrate and the optical wavelength conversion member to fix the optical wavelength conversion member to the photodetection substrate.

The X-ray detecting device may further include a first connection member adapted to electrically connect the X-ray detection panel and the driving circuit substrate and transmit signals between the X-ray detection panel and the driving circuit substrate.

The X-ray detecting device may further include a second connection member adapted to electrically connect the touch panel and the driving circuit substrate and transmit signals between the touch panel and the driving circuit substrate.

The touch panel may be selected from a capacitive overlay touch panel, a resistive overlay touch pattern, a surface acoustic wave touch panel, and an infrared beam touch panel.

The touch panel may include a transparent substrate and a touch sensor on the transparent substrate.

The touch panel may be configured to recognize a touch trajectory and to deliver information regarding the recognized touch trajectory to the driving circuit.

The optical wavelength conversion member may be a scintillator.

The photodetection substrate may include a photoelectric conversion panel having a number of elements arranged in a matrix, each element including a thin-film transistor and a photoelectric converter.

The thin-film transistor may include a gate electrode, a source electrode, and a drain electrode. The photoelectric converter may include a lower electrode electrically connected with a drain electrode of a corresponding thin-film transistor, an n-type semiconductor layer on the lower electrode, an intrinsic semiconductor layer on the n-type semiconductor layer, a p-type semiconductor layer on the intrinsic semiconductor layer, and an upper electrode on the p-type semiconductor layer.

The photodetection substrate may include a base substrate, a gate line on the base substrate, the gate line extending in a first direction, a gate electrode extending from the gate line, a gate insulating layer on the base substrate, the gate insulating layer covering the gate line and the gate electrode, a semiconductor layer on the gate insulating layer, a source electrode and a drain electrode on the semiconductor layer, a data line extending from the source electrode in a second direction intersecting with the first direction, a lower electrode extending from the drain electrode, a photosensor on the lower electrode, and an upper electrode on the photosensor.

The photosensor may be a PIN diode.

The X-ray detecting device may further include an X-ray interruption sheet between the driving circuit substrate and the X-ray detection panel, the X-ray interruption sheet being adapted to absorb X-rays penetrating the X-ray detection panel.

The X-ray detecting device may further include a light-generating sheet on the X-ray interruption sheet, the light-generating sheet being adapted to irradiate light to the X-ray detection panel.

The X-ray detecting device may further include a support plate beneath the X-ray detection panel to support the X-ray detection panel.

The lower case may include a bottom portion and lateral walls formed on a periphery of the bottom portion so that the lower case has a U-shaped configuration.

The upper case may be made of a light-transmitting material.

Embodiments are also directed to an X-ray imaging device including an X-ray generator, a collimator adapted to adjust an X-ray irradiation area by regulating a radiation range of X-rays emitted from the X-ray generator, an X-ray detecting device adapted to detect X-rays irradiated through the collimator, and a controller adapted to control the driving of the X-ray generator, the collimator, and the X-ray detecting device. The X-ray detecting device may include a lower case, a driving circuit substrate on the lower case, an X-ray detection panel on the driving circuit substrate and adapted to detect X-rays applied from the outside by converting the X-rays into electricity, a touch panel on the X-ray detection panel, and an upper case on the touch panel. The driving circuit substrate may be provided with a driving circuit. The driving circuit may be electrically connected with the X-ray detection panel and the touch panel and may be adapted to control the driving of the X-ray detection panel and the touch panel. A touch signal may be generated by the touch panel and a detection signal generated by the X-ray detection panel may be applied to the driving circuit. The driving circuit substrate may be connected with the controller.

The X-ray detection panel may include a photodetection substrate adapted to convert light into electricity and generate a detection signal, and an optical wavelength conversion member on the photodetection substrate, the optical wavelength conversion member being adapted to convert X-rays applied from the outside into light of a wavelength absorbed by the photodetection substrate.

The touch panel may be configured to recognize a touch trajectory and to deliver information regarding the recognized touch trajectory to the driving circuit.

The information regarding the touch trajectory delivered to the driving circuit may be delivered to the controller, and the controller may adjust the collimator so that X-rays are irradiated to an area recognized by the touch trajectory information.

Embodiments are also directed to an X-ray detecting device including a lower case, a driving circuit substrate on the lower case, a photodetection substrate connected with the driving circuit substrate and adapted to convert light into electricity and generate a detection signal, an optical wavelength conversion member on the photodetection substrate and adapted to convert X-rays applied from the outside into light of a wavelength that can be absorbed by the photodetection substrate, a touch panel on the optical wavelength conversion member, and an upper case on the touch panel. The driving circuit substrate may be provided with a driving circuit. The driving circuit may be electrically connected with the photodetection substrate and the touch panel, and is adapted to control the driving of the photodetection substrate and the touch panel. A touch signal generated by the touch panel and a detection signal generated by the photodetection substrate are applied to the driving circuit.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope thereof to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Throughout the description, the expression that a part is "connected" with another part not only means that they are "directly connected", but also that they are "electrically connected" via a different element in the middle. Furthermore, the expression that a part "includes" a component does not means that other components are excluded, but means that it can further include other components, unless otherwise indicated.

In the drawings, the thickness of respective components or films (layers) and areas has been exaggerated for clarity, and each device may have various additional devices that are not described herein. When a film (layer) is described as positioned on another film (layer) or substrate, it may be directly formed on the other film (layer) or substrate, or an additional film (layer) may be interposed between them.

Figure 1:
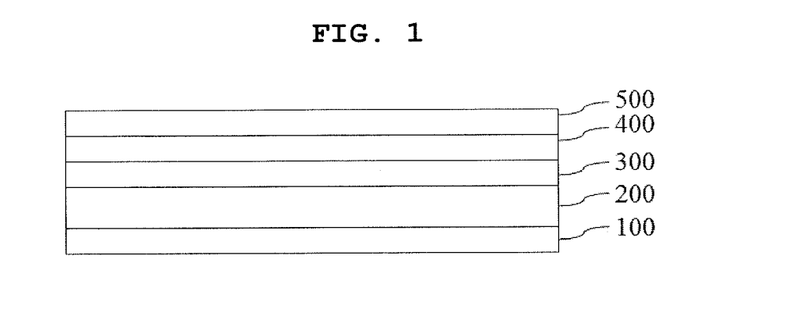
FIG. 1 illustrates a schematic structure of an X-ray detecting device according to an embodiment.

FIG. 1 illustrates a schematic structure of an X-ray detecting device according to an embodiment. As shown in FIG. 1, an X-ray detecting device according to an embodiment includes a lower case 100, a driving circuit substrate 200 arranged on the lower case, an X-ray detection panel 300 connected with the driving circuit substrate and adapted to convert X-rays, which are applied from the outside, into electricity to detect them, a touch panel 400 arranged on the X-ray detection panel, and an upper case 500 arranged on the touch panel.

The driving circuit substrate 200 is provided with a driving circuit, which is electrically connected with the X-ray detection panel 300 and the touch panel 400 to control the driving of the X-ray detection panel and the touch panel. Touch signals generated from the touch panel 400 and detection signals generated from the X-ray detection panel 300 are applied to the driving circuit.

The X-ray detecting device may include a first connection member for electrically connecting the X-ray detection panel 300 and the driving circuit substrate 200 and transmitting signals between the X-ray detection panel and the driving circuit substrate. The first connection member may be a flexible printed circuit board.

The X-ray detecting device may also include a second connection member for electrically connecting the touch panel 400 and the driving circuit substrate 200 and transmitting signals between the touch panel and the driving circuit substrate. The second connection member may be a flexible printed circuit board.

Figure 2:
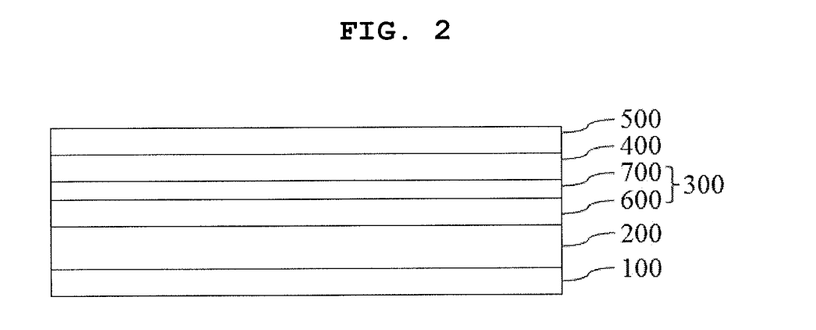
FIG. 2 illustrates a schematic structure of an X-ray detecting device according to another embodiment.

FIG. 2 illustrates a schematic structure of an X-ray detecting device according to another embodiment. As shown in FIG. 2, the X-ray detection panel 300 may include a photodetection substrate 600 adapted to convert light into electricity and generate detection signals and an optical wavelength conversion member 700 arranged on the photodetection substrate and adapted to convert X-rays, which are applied from the outside, into light of a wavelength that can be absorbed by the photodetection substrate.

Specifically, the X-ray detecting device shown in FIG. 2 includes a lower case 100, a driving circuit substrate 200 arranged on the lower case, a photodetection substrate 600 connected with the driving circuit substrate and adapted to convert light into electricity and generate detection signals, an optical wavelength conversion member 700 arranged on the photodetection substrate and adapted to convert X-rays, which are applied from the outside, into light of a wavelength that can be absorbed by the photodetection substrate, a touch panel 400 arranged on the optical wavelength conversion member, and an upper case 500 arranged on the touch panel. The driving circuit substrate 200 is provided with a driving circuit, which is electrically connected with the photodetection substrate 600 and the touch panel 400 to control the driving of the photodetection substrate 600 and the touch panel 400. Touch signals generated from the touch panel 400 and detection signals generated from the photodetection substrate 600 are applied to the driving circuit.

Embodiments will now be described in more detail with reference to specific examples. Repeated description of the same component will be omitted for clarity.

Figure 3:
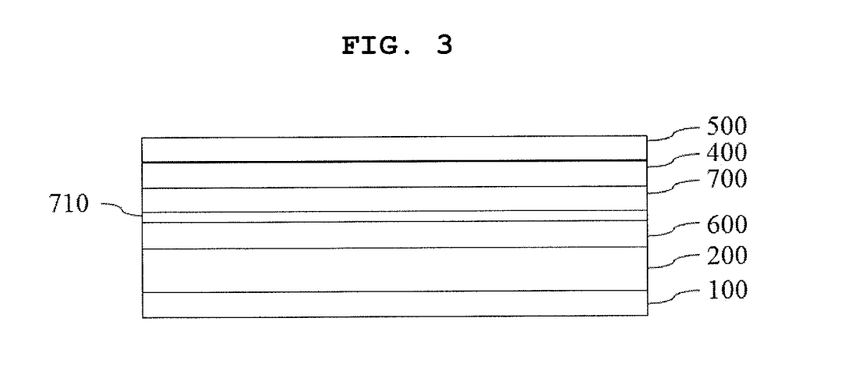
FIG. 3 illustrates a schematic structure of an X-ray detecting device according to still another embodiment.

FIG. 3 illustrates the structure of an X-ray detecting device according to an embodiment. The X-ray detecting device shown in FIG. 3 includes a lower case 100, a driving circuit substrate 200 arranged on the lower case, a photodetection substrate 600 connected with the driving circuit substrate and adapted to convert light into electricity and generate detection signals, an optical wavelength conversion member 700 arranged on the photodetection substrate and adapted to convert X-rays, which are applied from the outside, into light of a wavelength absorbed by the photodetection substrate, a touch panel 400 arranged on the optical wavelength conversion member, and an upper case 500 arranged on the touch panel. An adhesive layer 710 is arranged between the photodetection substrate 600 and the optical wavelength conversion member 700. The adhesive layer 710 is adapted to fix the optical wavelength conversion member 700 to the photodetection substrate 600.

The driving circuit substrate 200 is provided with a driving circuit, which is electrically connected with the photodetection substrate 600 and the touch panel 400 to control the driving of the photodetection substrate and the touch panel. Touch signals generated from the touch panel and detection signals generated from the photodetection substrate are applied to the driving circuit.

According to the present embodiment, the touch panel 400 may be of a type selected from a capacitive overlay type, a resistive overlay type, a surface acoustic wave type, and an infrared beam type. It will be assumed hereinafter, for clarity of description, that a touch panel of the capacitive overlay type is used. However, those skilled in the art can understand that touch panels of other types than the capacitive overlay type can also be used.

Figure 4:
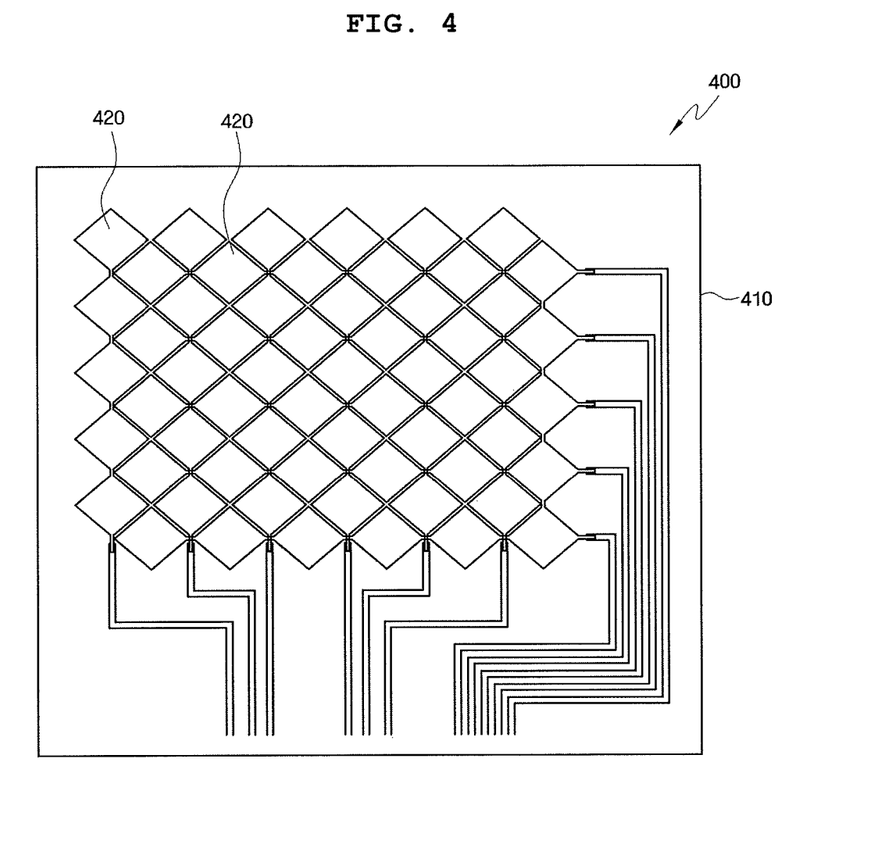
FIG. 4 illustrates a schematic structure of an exemplary touch panel used in an X-ray detecting device according to an embodiment.

FIG. 4 illustrates the structure of an exemplary touch panel 400. The touch panel includes a transparent substrate 410 and a touch sensor 420 formed on the transparent substrate. A touch panel of any suitable structures and type may be selected.

The touch panel 400 is adapted to recognize a touch trajectory. When the touch panel is touched by a finger, for example, information regarding the touched portion and information regarding the touch trajectory are delivered to the driving circuit of the driving circuit substrate 200.

The X-ray detecting device may be provided with a touch panel 400 so that, by touching the surface of the X-ray detecting device, a touch trajectory is generated. Information regarding the touch trajectory, which is recognized by the touch panel 400, is delivered to the driving circuit of the driving circuit substrate 200 and used as information for defining an X-ray irradiation area.

Figure 5A:
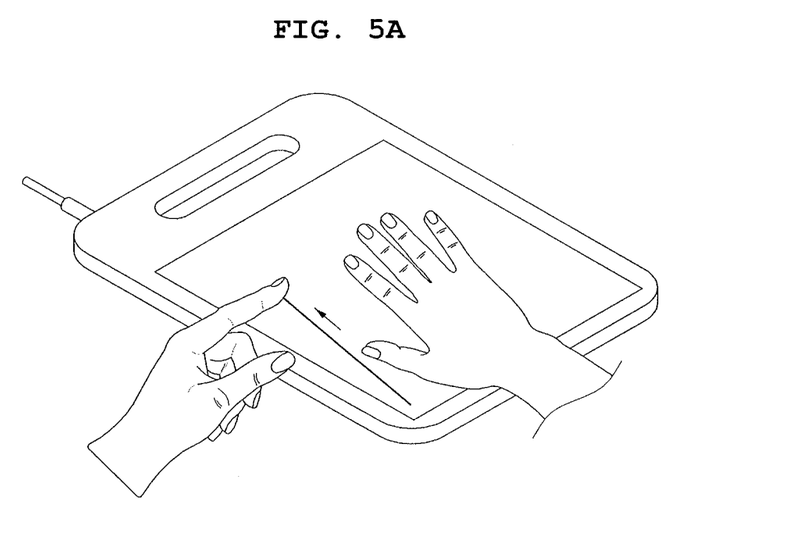
FIGS. 5A to 5C illustrate exemplary processes of marking an X-ray irradiation area, using a touch panel of an X-ray detecting device according to an embodiment.
Figure 5B:
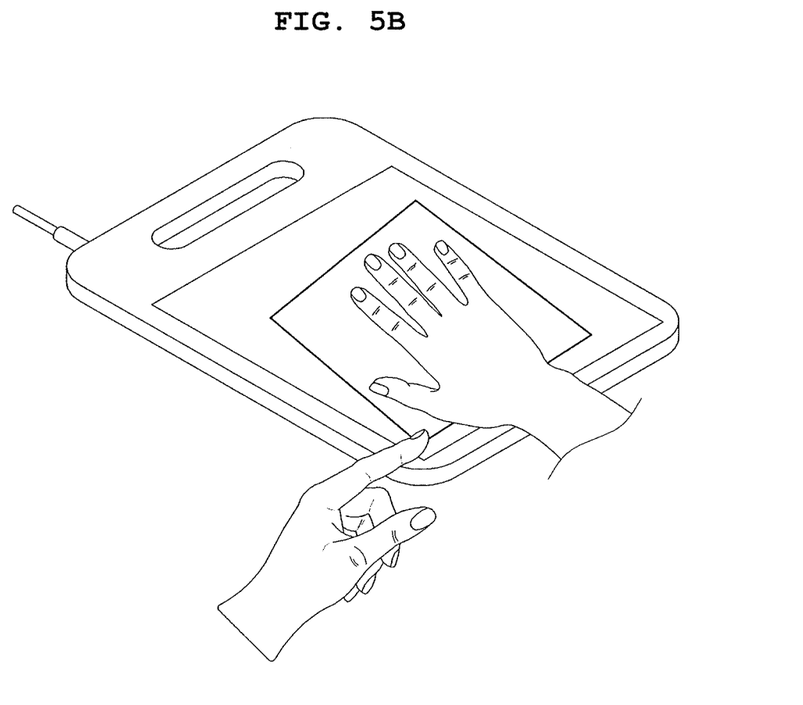
Figure 5C:
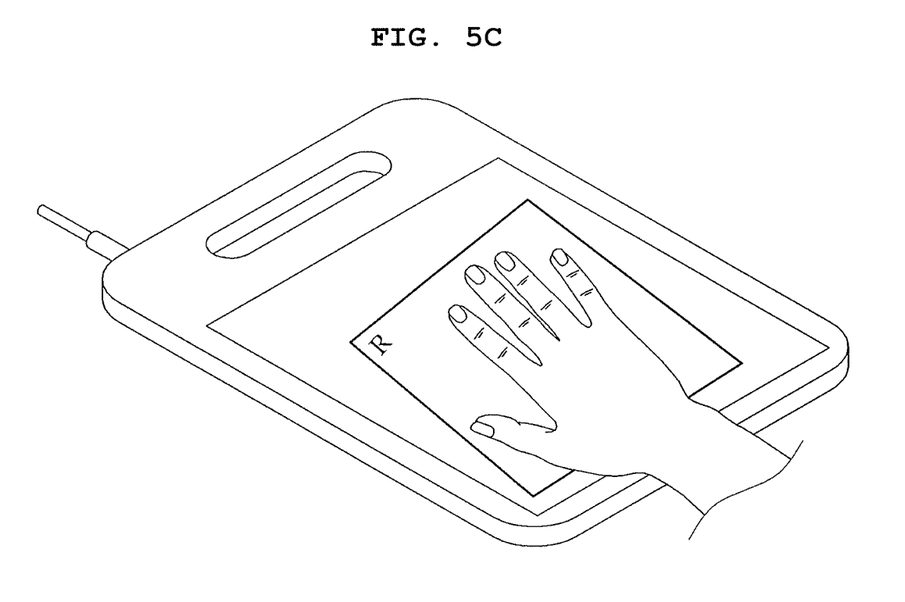

FIGS. 5A to 5C illustrate exemplary processes of marking an X-ray irradiation area, using a touch panel of an X-ray detecting device according to an embodiment.

Specifically, as shown in FIG. 5A, the hand of a patient, which is the target of X-ray imaging (hand at the right in FIG. 5A), is positioned on the X-ray detecting device. Then, the photographer drags his/her finger (see hand at the left in FIG. 5A) along the touch screen to select an area, to which X-rays are to be irradiated, to mark the X-ray irradiation area, which is indicated by a box in FIG. 5B. If necessary, brief information may be marked on the surface of the X-ray detecting device. FIG. 5C shows letter "R" inputted on the surface of the X-ray detecting device to indicate the right hand. Such marking of the X-ray irradiation area and input of brief information are enabled by the touch panel of the X-ray detecting device.

Information regarding the trajectory inputted to the touch panel 400 is delivered to the driving circuit of the driving circuit substrate 200, and then to the collimator of the X-ray imaging device. The collimator then adjusts the X-ray radiation range so that X-rays are irradiated only to the marked area. Specifically, the collimator has a shutter, which is adjusted to modify the range, to which X-rays from the X-ray generator are to be radiated. Such a collimator is widely known and used in the field of X-ray imaging devices, and detailed description of its structure and operation will be omitted herein.

Meanwhile, during readout after the X-ray imaging, X-ray readout is performed only in the designated and marked area. Such limitation of the readout area reduces readout time and the amount of data to be read. This makes storage and transmission of the data more convenient.

Therefore, the fact that the X-ray detecting device is provided with a touch panel enables the photographer to mark the X-ray irradiation area as desired and input or record desired information to record patient information intuitively.

The photodetection substrate 600 is adapted to absorb light applied from the outside, e.g. visible rays, and convert them into electricity, thereby detecting the light. For example, the photodetection substrate 600 may include a plurality of unit pixels DD arranged in a matrix or line type to detect different amounts of light depending on the position. Each unit pixel constitutes a photoelectric converter and defines a detection unit area. The photodetection substrate may have a thickness of about 0.5-2.5 mm.

The optical wavelength conversion member 700 is arranged on the photodetection substrate 600 to convert X-rays, which are applied from the outside, into light of a wavelength detectable by the photodetection substrate 600 and output the light. Specifically, the optical wavelength conversion member 700 may convert the X-rays into visible rays, e.g. green light, and provide the photodetection substrate 600 with the green light. The optical wavelength conversion member 700 may have a thickness of about 0.5-1.5 mm.

The optical wavelength conversion member 700 may be made of a scintillator, which is widely used in the art to convert X-rays into visible rays. Those skilled in the art can select and use a scintillator suited to a specific demand. The scintillator may be formed by growing scintillator crystals and may consist of, for example, column-forming crystals of CsI doped with thallium (Tl) or sodium (Na).

The optical wavelength conversion member 700 may be attached to the upper surface of the photodetection substrate 600 by an adhesive layer 710, which is formed on the lower surface. The adhesive layer 710 may have a thickness of about 0.1-1.0 mm.

At least one sealing member may be provided between the optical wavelength conversion member 700 and the photodetection substrate 600 to seal them. The sealing member may be arranged, for example, on a periphery between the optical wavelength conversion member 700 and the photodetection substrate 600.

The driving circuit substrate 200 is arranged on the lower case 100. The driving circuit substrate 200 may be fixed to the lower case 100 while being spaced from the lower surface of the lower case 100 by a plurality of driving circuit substrate supporters. The driving circuit substrate 200 may have a thickness of about 1.0-5.0 mm.

The driving circuit substrate 200 is electrically connected with the photodetection substrate 600 and the touch panel 400, respectively, and is adapted to control the driving of the photodetection substrate 600 and the touch panel 400. The driving circuit substrate 200 is adapted to receive detection signals from the photodetection substrate 600, analyze the detection signals, generate data of the amount of light detected by the unit pixels DD, and store the data.

The lower and upper cases 100 and 500 contain and protect the above-described components, i.e. the driving circuit substrate 200, the photodetection substrate 600, the optical wavelength conversion member 700, the touch panel 400, etc.

Although not shown in the drawings, a separate sealing member may be provided on extensions from peripheries of the lower and upper cases 100 and 500 to seal the peripheries of the lower and upper cases 100 and 500 and contain and protect the components.

The upper case 500 has the shape of a flat plate. Specifically, the upper case 500 is made of a light-transmitting material so that X-rays penetrate it.

The photodetection substrate 600 will now be described in detail.

Referring to FIGS. 6 through 9, the photodetection substrate 600 includes a photoelectric conversion panel 601 having a number of thin-film transistors (TFT) 605 and photoelectric converters (Pd) 606 arranged in a matrix type.

The TFT includes a gate electrode 621, a source electrode 651, and a drain electrode 661. The photoelectric converter 606 includes a lower electrode 660 electrically connected with the drain electrode 661 of the TFT, an n-type semiconductor layer 671 formed on the lower electrode, an intrinsic semiconductor layer 672 formed on the n-type semiconductor layer, a p-type semiconductor layer 673 formed on the intrinsic semiconductor layer, and an upper electrode 680 formed on the p-type semiconductor layer.

Figure 8:
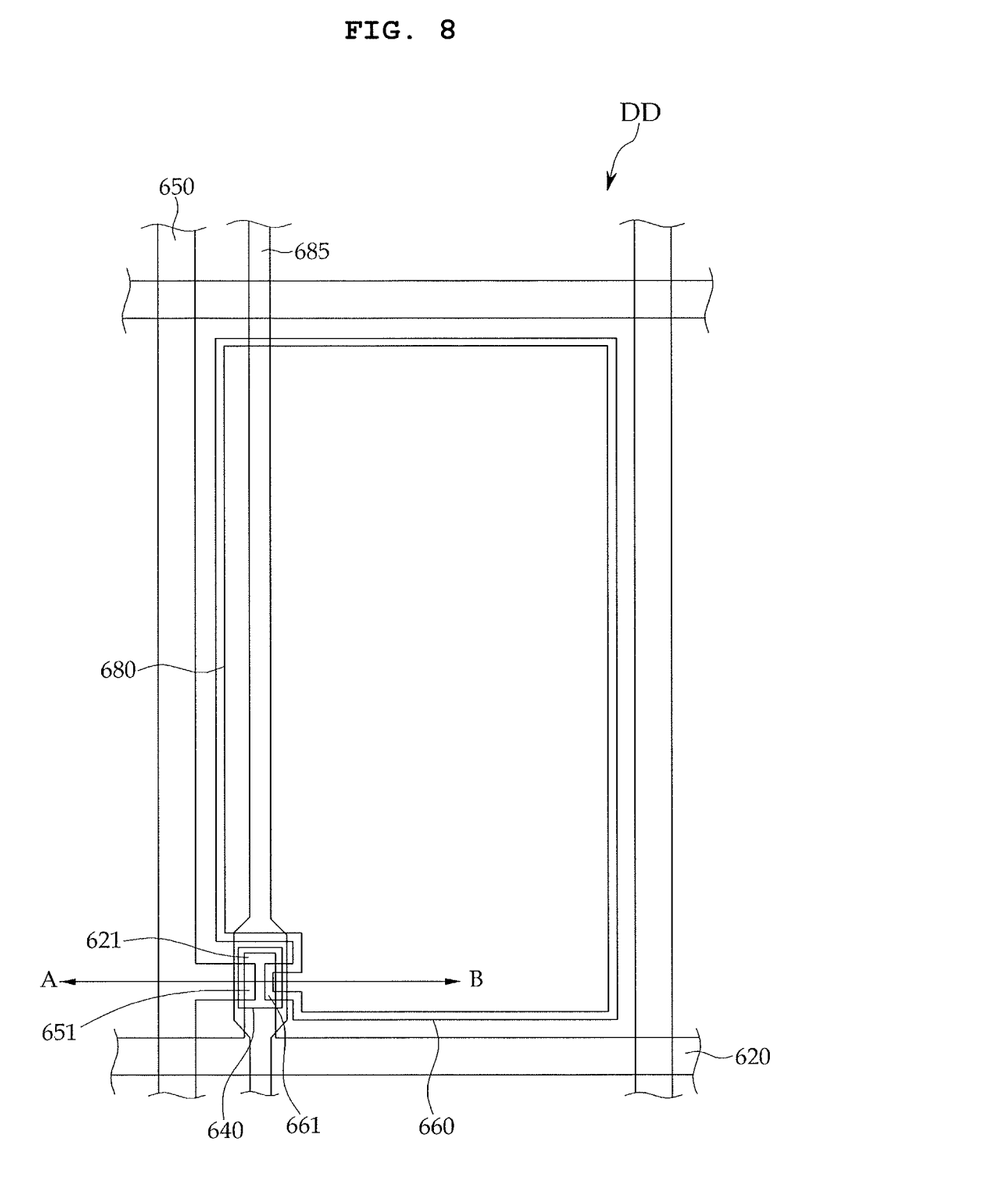
FIG. 8 illustrates a schematic construction of a detection unit area DD of the photodetection substrate shown in FIG. 6.
Figure 9:
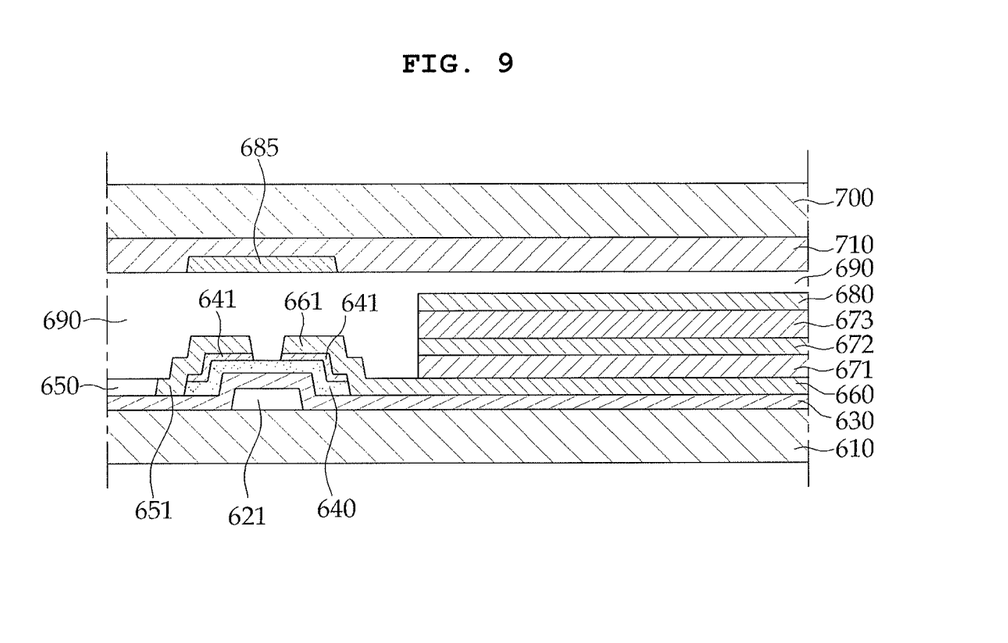
FIG. 9 is a sectional view taken along line A-B of FIG. 8.

Referring to FIGS. 8 and 9, the photodetection substrate 600 includes a base substrate 610, a gate line 620 formed on the base substrate so as to extend in a first direction, a gate electrode 621 extending from the gate line, a gate insulating layer 630 formed on the base substrate so as to cover the gate line and the gate electrode, a semiconductor layer 640 formed on the gate insulating layer, source and drain electrodes 651 and 661 formed on the semiconductor layer, a data line 650 formed so as to extend from the source electrode in a second direction, which intersects with the first direction, a lower electrode 660 formed so as to extend from the drain electrode, a photosensor formed on the lower electrode, and an upper electrode 680 formed on the photosensor.

The photosensor corresponds to the photoelectric converter 606. A PIN diode may be used as the photosensor. The PIN diode includes an n-type semiconductor layer 671 formed on the lower electrode 660, an intrinsic semiconductor layer 672 formed on the n-type semiconductor layer, and a p-type semiconductor layer 673 formed on the intrinsic semiconductor layer.

Figure 6:
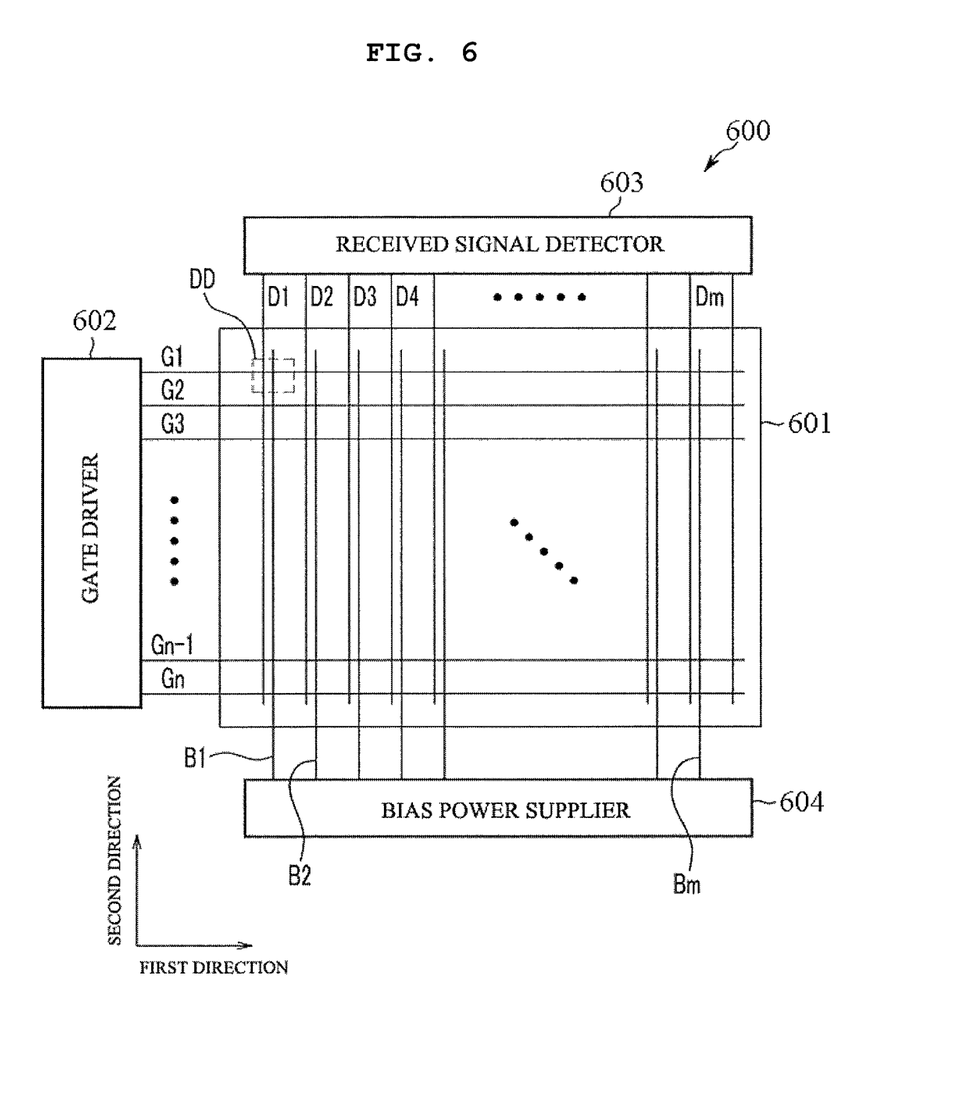
FIG. 6 illustrates a schematic construction of an exemplary photodetection substrate used in an X-ray detecting device according to an embodiment.

Specifically, FIG. 6 is a block diagram showing the structure of the photodetection substrate 600 of the X-ray detecting device according to the present embodiment.

Referring to FIG. 6, the photodetection substrate 600 according to the present embodiment includes a photoelectric conversion panel 601, a gate driver 602, a received signal detector 603, and a bias power supplier 604.

The photoelectric conversion panel 601 includes a plurality of signal lines G1-Gn, D1-Dm, B1-Bm and a plurality of detection unit elements DD connected with the signal lines and arranged in an approximately matrix type.

Each detection unit element DD includes a TFT and a photoelectric converter 606 as a photosensor. As the photosensor, a photodiode Pd having excellent photoelectric conversion characteristics may be used, such as a PIN diode. It will be assumed in the following description that a PIN diode is used as the photosensor. The detection unit element DD will be described below in detail with reference to FIGS. 6-9.

The signal lines G1-Gn, D1-Dm, B1-Bm include a plurality of gate lines G1-Gn adapted to deliver gate signals (also referred to as scan signals), a plurality of data lines D1-Dm adapted to deliver signals detected by the PIN diodes to the received signal detector 603, and bias lines B1-Bm adapted to apply a bias voltage to each PIN diode.

The gate lines G1-Gn extend in the row direction and are approximately parallel with each other. In the present embodiment, the direction of extension of the gate lines will be referred to as a first direction (refer to FIG. 6).

The data lines D1-Dm and the bias lines B1-Bm extend in the column direction and are approximately parallel with each other. In the present embodiment, the direction of extension of the data and bias lines will be referred to as a second direction (refer to FIG. 6).

The gate driver 602 is connected with the gate lines G1-Gn of the photoelectric conversion panel 601 and is adapted to apply gate signals to gate electrodes of TFTs provided inside the detection unit elements DD. The gate signals refer to signals for controlling the turn-on or turn-off of the TFTs, and are transmitted through the gate lines G1-Gn. The gate signals include gate ON voltage Von signals for turning on the TFTs and gate OFF voltage Voff signals for turning off the TFTs. The gate driver 602 is applied to successively apply gate ON voltage Von signals to respective gate lines G1-Gn and apply gate OFF voltage Voff signals while no gate ON voltage Von is applied.

The received signal detector 603 is connected to the data lines D1-Dm of the photoelectric conversion panel 601 and is adapted to receive signals detected by the PIN diodes. The received signal detector 603 collects signals, which are detected by the PIN diodes, during gate ON time at a capacitor (not shown) connected with an OP amp (not shown). The received signal detector 603 then transmits the collected signals to a shift register (not shown), stores them for at least one gate ON time, and transmits them to an AD converter (not shown). The signals transmitted to the AD converter (not shown) are converted into digital signals and outputted. The finally outputted digital signals are displayed on a digital screen.

The bias power supplier 604 is connected to the bias lines B1-Bm of the photoelectric conversion panel 601 and is adapted to apply a bias voltage to the PIN diodes. The PIN diodes, to which a bias voltage is applied, can detect visible rays, which correspond to irradiated X-rays, i.e. which have been converted from X-rays through the optical wavelength conversion member (scintillator), and generate a current corresponding to the detected visible rays. When no bias voltage is applied, the PIN diodes generate no current, even if visible rays are incident, i.e. do not play the role of photosensors.

Each of the driving devices 602, 603, and 604 may be integrated and mounted on the photoelectric conversion panel 601 as an IC chip. Alternatively, the driving devices 602, 603, and 604 may be mounted on flexible printed circuit film (not shown) and attached to the photoelectric conversion panel 601 as a TCP (Tape Carrier Package), or mounted on a separate printed circuit board (not shown).

Figure 7:
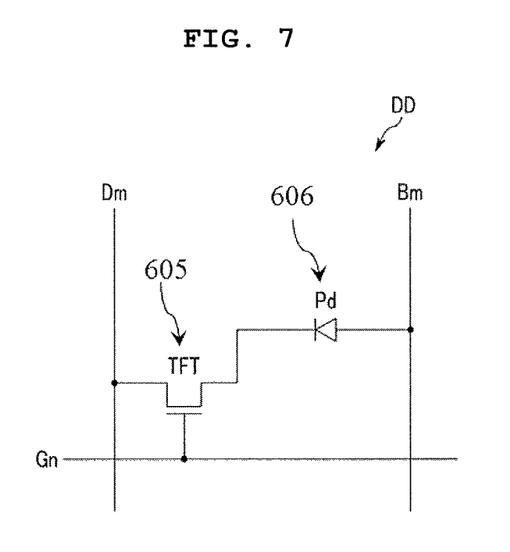
FIG. 7 illustrates an equivalent circuit of a detection unit area DD of the photodetection substrate shown in FIG. 6.

FIG. 7 illustrates an equivalent circuit of the detection unit element DD of FIG. 6. Referring to FIG. 7, the detection unit element DD includes a TFT 605 and a photoelectric converter (Pd) 606, which is a photosensor. It is assumed in the example shown in FIG. 7 that a PIN diode is used as the photosensor 201.

The PIN diode plays the role of a photosensor for sensing light. A scintillator is positioned on the TFT and the PIN diode as the optical wavelength conversion member 700. The scintillator consists of a material that collides with irradiation and emits light so that, when X-rays are incident, they are converted into light in the visible range and emitted. The emitted visible rays are sensed by the PIN diode, which is a photosensor.

The TFT, in response to a gate signal Gn, transmits an optical signal, which is sensed and outputted by the PIN diode, to the received signal detector 603 through the data line Dm.

FIG. 8 illustrates the arrangement and construction of the detection unit element DD shown in FIG. 7. Referring to FIG. 8, a detection unit element DD provided inside a photodetection substrate 600 according to the present embodiment is connected with a data line 650, a bias line 685, and a gate line 620.

The data line 650 delivers a data signal Dm and extends in the second direction.

The bias line 685 delivers a bias voltage Bm and extends in the second direction. The bias line 685 is provided with a contact hole (not shown), through which the bias line 685 and the PIN diode Pd are connected.

The gate line 620 delivers a gate signal Gn and extends in a direction (first direction) intersecting with the data line 650 or the bias line 685. The gate line 620 contacts the gate electrode 621 through a contact hole (not shown).

FIG. 9 is a sectional view taken along line A-B of FIG. 8. Referring to FIGS. 8 and 9, a gate line 620 is formed on a base substrate 610, which is made of transparent glass or plastic, for example, and is connected with a gate electrode 621.

A gate insulating layer 630 is formed on the gate line 620 and the gate electrode 621. The gate insulating layer 630 is made of an insulating material, such as silicon nitride ($SiN_x$) or silicon oxide ($SiO_x$).

A semiconductor layer 640 is formed on the gate insulating layer 630 using a material such as hydrogenated amorphous silicon or polysilicon. The semiconductor layer 640 is formed over the gate electrode 621 and in a partial area of the gate insulating layer 630. The semiconductor layer 640 preferably has a size large enough to cover both ends of the gate electrode 621.

An ohmic contact member 641 is formed on the semiconductor layer 640. The ohmic contact member 641 may be made of n+ hydrogenated amorphous silicon, which is doped with a high concentration of n-type impurities (e.g. phosphorus (P)), or silicide. The ohmic contact member 641 is positioned between the semiconductor layer 640 and source and drain electrodes 651 and 661 to reduce contact resistance between them.

The source electrode 651 is formed on the gate insulating layer 630 and the ohmic contact member 641, which is formed on the left side in FIG. 9. The source electrode 651 is connected with the data line 650.

The drain electrode 651 is separated from the data line 650 and is positioned opposite the source electrode 651 with the gate electrode 621 interposed between them. The drain electrode 661 is formed on the gate insulating layer 630 and the ohmic contact member 641, which is formed on the right side.

The drain electrode 661 is extended to form a lower electrode 660. The lower electrode 660, including the drain electrode 661, is formed in an area of the semiconductor layer 640, which forms the TFT, i.e. in an area where the PIN diode is arranged. That is, an extension of the drain electrode 661 defines the lower electrode 660 of the PIN diode.

A gate electrode 621, a source electrode 651, and a drain electrode 661 constitute, together with a semiconductor layer 640, a TFT, which has a channel formed on the semiconductor layer 640 between the source and drain electrodes 651 and 661.

The PIN diode, which is a photosensor, has semiconductor layers 671, 672, and 673 formed on the lower electrode 660. Specifically, the PIN diode has an n-type semiconductor layer 671, an intrinsic semiconductor layer 672, and a p-type semiconductor layer 673 stacked successively.

The PIN diode has an upper electrode 680 formed on the semiconductor layers 671, 672, and 673 using a transparent conductive material, such as ITO or IZO. The upper electrode 680 is formed in an area corresponding to the lower electrode 660 and the semiconductor layers 671, 672, and 673 of the PIN diode.

A protective layer 690 is then formed. The protective layer 690 is formed on the drain electrode 661 that is connected with the data line 650, on the exposed semiconductor layer 640, and on the upper electrode 680 of the PIN diode. The protective layer 690 may be made of an inorganic or organic insulating material, such as silicon nitride or silicon oxide. Alternatively, the protective layer 690 may have a double-layered structure, which is obtained by stacking layers of inorganic or organic material. A contact hole (not shown) is formed on the protective layer 690 to expose the upper electrode 680. A bias line 685 is also formed on the protective layer 690.

An adhesive layer 710 is arranged on the protective layer 690 and the bias line 685. An optical wavelength conversion member 700 is formed on the adhesive layer using a scintillator.

Although not shown in the drawings, an upper case 500 is arranged on the scintillator 600. The upper case is made of a light-transmitting material.

Figure 10:
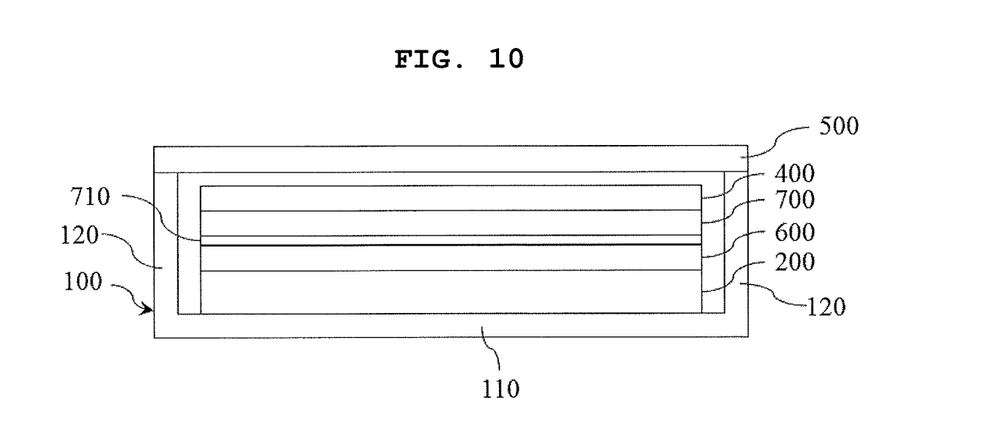
FIG. 10 illustrates a schematic structure of an X-ray detecting device according to another embodiment.

FIG. 10 illustrates an X-ray detecting device according to another embodiment. The X-ray detecting device shown in FIG. 10 has the same construction as in the case of Embodiment 1, except for the structure of the lower and upper cases 100 and 500.

In the present embodiment, the lower case 100 has a U-shaped configuration and includes a bottom portion 110 and lateral walls 120 formed on the periphery of the bottom portion. Specifically, the lower case 100 includes a bottom portion 110 and lateral walls 120 formed on the periphery of the bottom portion 110 to define a containing space, in which all of the components are contained. The upper case 500 is connected to the upper ends of the lateral walls 120 to cover the opening of the lower case 100 and seal the containing space. X-rays, applied from the outside, then penetrate the upper case 500 and reach the optical wavelength conversion member 700 through the touch panel 400. The lower case may be made of a carbon plate, for example, and may have a thickness of about 1.0-5.0 mm. The upper case 500 is made of a light-transmitting material and may have a thickness of about 1.0-3.0 mm.

Figure 11:
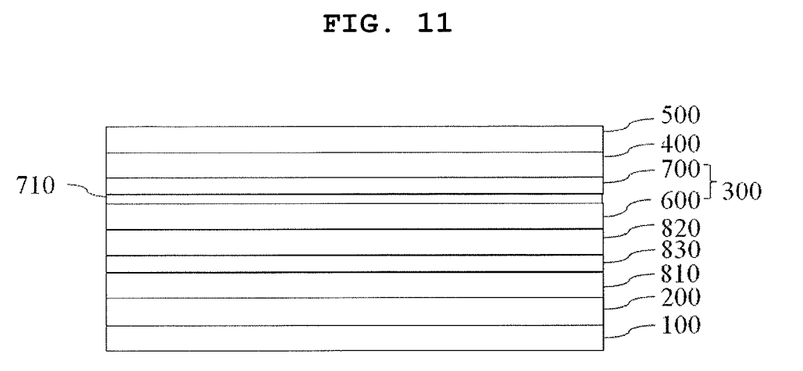
FIG. 11 illustrates a schematic structure of an X-ray detecting device according to still another embodiment.

FIG. 11 illustrates an X-ray detecting device according to still another embodiment. The X-ray detecting device shown in FIG. 11 has the same construction as in the case of Embodiment 1, except that it further includes an X-ray interruption sheet 810, a support plate 820, and a light-generating sheet 830.

The X-ray interruption sheet 810 is arranged between the driving circuit substrate 200 and the optical wavelength conversion member 700 of the X-ray detection panel 300 so that, parts of X-rays, which have been applied from the outside, and which have passed without being converted into visible rays by the optical wavelength conversion member 700 of the X-ray detection panel 300, are prevented from reaching the driving circuit substrate 200. The X-ray interruption sheet 810 according to the present embodiment includes at least one of gold (Au) and lead (Pb) to absorb and interrupt the X-rays. Specifically, the X-ray interruption sheet 810 may have a thickness of about 1.5 mm or less, for example.

A support plate 820 is positioned beneath the photodetection substrate 600 of the X-ray detection panel 300 to support the X-ray detection panel 300.

Specifically, the support plate 820 is arranged beneath the photodetection substrate 600 to support the photodetection substrate 600. The support plate 820 may be made of a transparent material, e.g. glass, or a synthetic resin such as acrylate. Although not shown in the drawings, adhesive film may be arranged on the upper surface of the support plate 820 to attach the photodetection substrate 600 to the upper surface of the support plate 820. The support plate 820 may have a thickness of about 2-5 mm. The adhesive film may have a thickness of about 0.1-1.0 mm.

A light-generating sheet 830 is positioned on the X-ray interruption sheet 810 to irradiate light to the photodetection substrate 600 of the X-ray detection panel 300.

Specifically, the light-generating sheet 830 may be positioned on the X-ray interruption sheet 810 while being spaced downwards from the support plate 820. The light-generating sheet 830 can generate light of the same luminance from the entire upper surface, and light generated by the light-generating sheet 830 passes through the support plate 820 and reaches the photodetection substrate 600. As a result, the unit pixels DD of the photodetection substrate 600 can be saturated in the same condition. The light-generating sheet 830 may have a thickness of about 0.1-1.5 mm.

Although not shown in the drawings, a separate support member may be arranged between the driving circuit substrate 200 and the X-ray interruption sheet 810. In this case, separate adhesive film may be provided on the lower surface of the X-ray interruption sheet 810 to attach the X-ray interruption sheet 810 to the upper surface of the support member.

Figure 12:
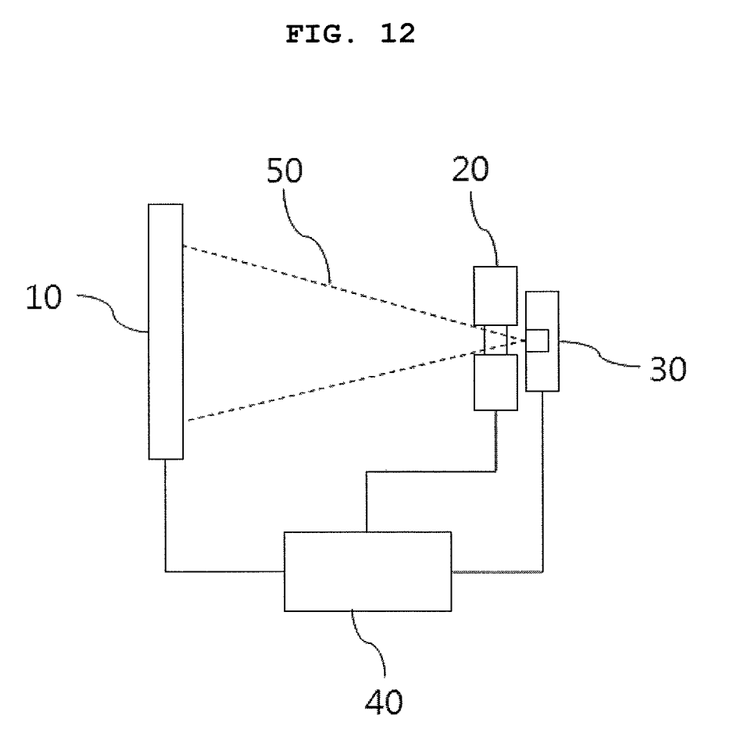
FIG. 12 illustrates a schematic structure of an X-ray imaging device according to an embodiment.

As shown in FIG. 12, an X-ray imaging device according to an embodiment may include an X-ray generator 30, a collimator 20 adapted to adjust the X-ray irradiation area by modifying the irradiation range of X-rays 50 emitted from the X-ray generator 30, an X-ray detecting device 10 adapted to detect X-rays irradiated through the collimator 20, and a controller 40 adapted to control the driving of the X-ray generator 30, the collimator 20, and the X-ray detecting device 10. The X-ray detecting device 10 in this embodiment is the same X-ray detecting device as described in previous embodiments.

Specifically, the X-ray detecting device includes a lower case 100, a driving circuit substrate 200 arranged on the lower case, an X-ray detection panel 300 connected with the driving circuit substrate and adapted to convert X-rays, which are applied from the outside, into electricity to detect them, a touch panel 400 arranged on the X-ray detection panel, and an upper case 500 arranged on the touch panel.

The driving circuit substrate 200 is provided with a driving circuit, which is electrically connected with the X-ray detection panel 300 and the touch panel 400 to control the driving of the X-ray detection panel and the touch panel. Touch signals generated from the touch panel 400 and detection signals generated from the X-ray detection panel 300 are applied to the driving circuit. The driving circuit substrate 200 is connected with the controller.

The X-ray detection panel 300 includes a photodetection substrate 600 adapted to convert light into electricity and generate detection signals and an optical wavelength conversion member 700 arranged on the photodetection substrate and adapted to convert X-rays, which are applied from the outside, into light of a wavelength absorbed by the photodetection substrate.

By way of summation and review, when X-rays are used clinically, it is desirable to designate a target area to which X-rays are to be irradiated, so that X-rays are directed only to the corresponding part. This may prevent the patient from being excessively exposed to X-rays and may guarantee that only the desired part is exposed to X-rays. A collimator is used to restrict such an irradiation area.

In order to guarantee that X-rays are irradiated only to the corresponding part, the patient's affected area is positioned on an X-ray detecting device, and a collimator, which is arranged near the X-ray generator of the X-ray imaging device, is adjusted. In typical clinical situations, the shutter arranged on the collimator is manually adjusted to regulate the radiation range of X-rays passing through the collimator so as to regulate the irradiation area. Particularly, the X-ray photographer checks the position to which X-rays are to be irradiated, and adjusts the collimator shutter, and then again checks whether the X-ray irradiation area has been adjusted correctly. Recalibration is needed if the X-ray irradiation position has failed to be adjusted correctly. Such manual adjustment of the X-ray irradiation position and designation of the X-ray irradiation area may cause inconveniences. Furthermore, information regarding the X-ray irradiation area is not associated with the X-ray detecting device, and thus, when detection results are displayed after X-ray irradiation, readout is performed throughout the entire area of the X-ray detecting device. This increases the amount of X-ray readout data, and thus delays the readout time and the display time.

Embodiments may provide an X-ray detecting device having a touch panel, which may enable an X-ray photographer to directly mark an X-ray irradiation area on the touch panel and thus easily designate and check the X-ray irradiation area. The touch panel 400 of the X-ray imaging device may recognizes a touch trajectory on the touch panel, and information regarding the recognized touch trajectory may be delivered to the driving circuit. The information regarding the touch trajectory may be delivered from the driving circuit to the controller, which then adjusts the collimator so that X-rays are irradiated to the area recognized based on the touch trajectory information. The touch trajectory defines the X-ray irradiation area.

The X-ray imaging device according to embodiments, when employed, may make it very easy to mark the X-ray irradiation area simply by dragging the top of the touch panel of the X-ray detecting device. In addition, X-ray readout is performed only on the above marked area, which reduces the readout time and the amount of data to be read. Therefore, when used clinically, the X-ray imaging device according to embodiments lessens the workload on the X-ray photographer, who would otherwise have to retain the patient's affected area on the X-ray detecting device, approach the collimator, designate the X-ray irradiation area, and correct the X-ray irradiation area again, and reduces the X-ray readout time after the imaging process, as well as time to store and transmit data.

Based on the trajectory information from the touch panel, the controller adjusts the collimator so that X-rays are irradiated only to the designated area. Furthermore, the fact that X-ray imaging information needs to be detected only with regard to the designated area shortens detection time, as well as time to store and transmit detected information.

Therefore, the X-ray detecting device having a touch panel according to the embodiments makes it easy to mark an area, to which X-rays are to be irradiated, using the touch panel.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims

What is claimed is:

1. An X-ray detecting device, comprising:
   a lower case;
   a driving circuit substrate on the lower case;
   a collimator to adjust an X-ray irradiation area by regulating a radiation range of X-rays emitted from an outside;
   an X-ray detection panel connected with the driving circuit substrate, the X-ray detection panel to detect X-rays applied from the collimator by converting the X-rays into electricity;
   a touch panel on the X-ray detection panel; and
   an upper case on the touch panel, wherein:
   the driving circuit substrate is provided with a driving circuit,
   the driving circuit is electrically connected with the X-ray detection panel and the touch panel, and is to control the driving of the X-ray detection panel, the collimator and the touch panel,
   the X-rays from the outside reach the X-ray detection panel through the touch panel,
   the touch panel recognizes a touch trajectory defining an X-ray irradiation area of the touch panel, and delivers information regarding the recognized touch trajectory to the driving circuit, and
   the driving circuit adjusts the collimator so that X-rays are irradiated to the X-ray irradiation area of the touch panel recognized by the touch trajectory information.

2. The X-ray detecting device as claimed in claim 1, wherein the X-ray detection panel includes:
   a photodetection substrate to convert light into electricity and generate a detection signal; and
   an optical wavelength conversion member on the photodetection substrate, the optical wavelength conversion member to convert X-rays applied from an outside into light of a wavelength that can be absorbed by the photodetection substrate.

3. The X-ray detecting device as claimed in claim 2, wherein an adhesive layer is between the photodetection substrate and the optical wavelength conversion member to fix the optical wavelength conversion member to the photodetection substrate.

4. The X-ray detecting device as claimed in claim 2, wherein the optical wavelength conversion member is a scintillator.

5. The X-ray detecting device as claimed in claim 3, wherein the photodetection substrate includes:
   a base substrate;
   a gate line on the base substrate, the gate line extending in a first direction;
   a gate electrode extending from the gate line;
   a gate insulating layer on the base substrate, the gate insulating layer covering the gate line and the gate electrode;
   a semiconductor layer on the gate insulating layer;
   a source electrode and a drain electrode on the semiconductor layer;
   a data line extending from the source electrode in a second direction intersecting with the first direction;
   a lower electrode extending from the drain electrode;
   an n-type semiconductor layer on the lower electrode;
   an intrinsic semiconductor layer on the n-type semiconductor layer;
   a p-type semiconductor layer on the intrinsic semiconductor layer;
   an upper electrode on the p-type semiconductor layer;
   a protective layer on the source electrode, the drain electrode, the semiconductor layer, and the upper electrode, the protective layer having a contact hole exposing the upper electrode; and
   a bias line on the protective layer, the bias line having a contact hole through which the bias line is connected to a photosensor including the n-type semiconductor layer, the intrinsic semiconductor layer, and the p-type semiconductor layer.

6. The X-ray detecting device as claimed in claim 2, wherein the photodetection substrate includes a photoelectric conversion panel having a number of elements arranged in a matrix, each element including a thin-film transistor and a photoelectric converter.

7. The X-ray detecting device as claimed in claim 6, wherein:
   the thin-film transistor includes a gate electrode, a source electrode, and a drain electrode, and
   the photoelectric converter includes:
      a lower electrode electrically connected with a drain electrode of a corresponding thin-film transistor;
      an n-type semiconductor layer on the lower electrode;
      an intrinsic semiconductor layer on the n-type semiconductor layer;
      a p-type semiconductor layer on the intrinsic semiconductor layer; and
      an upper electrode on the p-type semiconductor layer.

8. The X-ray detecting device as claimed in claim 1, further comprising a first connection member electrically connecting the X-ray detection panel and the driving circuit substrate, and transmitting signals between the X-ray detection panel and the driving circuit substrate.

9. The X-ray detecting device as claimed in claim 1, further comprising a second connection member electrically connecting the touch panel and the driving circuit substrate, and to transmit signals between the touch panel and the driving circuit substrate.

10. The X-ray detecting device as claimed in claim 1, wherein the touch panel is selected from a capacitive overlay touch panel, a resistive overlay touch pattern, a surface acoustic wave touch panel, and an infrared beam touch panel.

11. The X-ray detecting device as claimed in claim 1, wherein the touch panel includes a transparent substrate and a touch sensor on the transparent substrate.

12. The X-ray detecting device as claimed in claim 1, further comprising an X-ray interruption sheet between the driving circuit substrate and the X-ray detection panel, the X-ray interruption sheet to absorb X-rays penetrating the X-ray detection panel.

13. The X-ray detecting device as claimed in claim 12, further comprising a light-generating sheet on the X-ray interruption sheet, the light-generating sheet to irradiate light to the X-ray detection panel.

14. The X-ray detecting device as claimed in claim 1, further comprising a support plate beneath the X-ray detection panel to support the X-ray detection panel.

15. The X-ray detecting device as claimed in claim 1, wherein the lower case includes a bottom portion and lateral walls formed on a periphery of the bottom portion so that the lower case has a U-shaped configuration.

16. The X-ray detecting device as claimed in claim 1, wherein the upper case is made of a light-transmitting material.

17. An X-ray imaging device, comprising:
an X-ray generator;
a collimator to adjust an X-ray irradiation area by regulating a radiation range of X-rays emitted from the X-ray generator;
an X-ray detecting device to detect X-rays irradiated through the collimator; and
a controller to control the driving of the X-ray generator, the collimator, and the X-ray detecting device, wherein the X-ray detecting device includes:
a lower case;
a driving circuit substrate on the lower case;
an X-ray detection panel on the driving circuit substrate, the X-ray detection panel to detect X-rays applied from the collimator by converting the X-rays into electricity;
a touch panel on the X-ray detection panel; and
an upper case on the touch panel, wherein:
the driving circuit substrate is provided with a driving circuit,
the driving circuit is electrically connected with the X-ray detection panel and the touch panel, and is to control the driving of the X-ray detection panel and the touch panel,
a touch signal generated by the touch panel and a detection signal generated by the X-ray detection panel are applied to the driving circuit,
the driving circuit substrate is connected with the controller,
the X-rays from the collimator reach the X-ray detection panel through the touch panel,
the touch panel recognizes a touch trajectory, and delivers information regarding the recognized touch trajectory to the driving circuit,
the information regarding the touch trajectory delivered to the driving circuit is delivered to the controller, and
the controller adjusts the collimator so that X-rays are irradiated to an area recognized by the touch trajectory information, wherein
the X-ray detection panel includes:
a photodetection substrate to convert light into electricity and generate a detection signal; and
an optical wavelength conversion member on the photodetection substrate, the optical wavelength conversion member to convert X-rays applied from the collimator into light of a wavelength absorbed by the photodetection substrate, wherein
the photodetection substrate includes:
a base substrate;
a gate line on the base substrate, the gate line extending in a first direction;
a gate electrode extending from the gate line;
a gate insulating layer on the base substrate, the gate insulating layer covering the gate line and the gate electrode;
a semiconductor layer on the gate insulating layer;
a source electrode and a drain electrode on the semiconductor layer;
a data line extending from the source electrode in a second direction intersecting with the first direction;
a lower electrode extending from the drain electrode;
a photosensor on the lower electrode; and
an upper electrode on the photosensor.

18. An X-ray detecting device, comprising:
a lower case;
a driving circuit substrate on the lower case;
a collimator to adjust an X-ray irradiation area by regulating a radiation range of X-rays emitted from an outside;
a photodetection substrate connected with the driving circuit substrate to convert light into electricity and generate a detection signal;
an optical wavelength conversion member on the photodetection substrate to convert X-rays applied from the collimator into light of a wavelength that can be absorbed by the photodetection substrate;
a touch panel on the optical wavelength conversion member; and
an upper case on the touch panel, wherein:
the driving circuit substrate is provided with a driving circuit,
the driving circuit is electrically connected with the photodetection substrate and the touch panel, and to control the driving of the photodetection substrate and the touch panel,
a touch signal generated by the touch panel and a detection signal generated by the photodetection substrate are applied to the driving circuit, the X-rays from the outside reach the optical wavelength conversion member through the touch panel,
the touch panel detects a touch trajectory, and delivers information regarding the detected touch trajectory to the driving circuit, the information regarding the detected touch trajectory including first information associated with the X-ray irradiation area and second information noted on the touch panel by a user, and the driving circuit adjusts the collimator according to the first information associated with the X-ray irradiation area.

19. The X-ray detecting device as claimed in claim 18, wherein:
the touch trajectory includes a first touch trajectory associated with the first information, the first touch trajectory defining the X-ray irradiation area, and a second touch trajectory associated with the second information, and
the second touch trajectory is inside of the first touch trajectory defining the X-ray irradiation area.

* * * * *